(12) United States Patent
Kim et al.

(10) Patent No.: US 8,372,453 B2
(45) Date of Patent: Feb. 12, 2013

(54) COMPOSITION FOR PREVENTION OR TREATMENT OF INSOMNIA

(75) Inventors: Jae-Soo Kim, Goyang-si (KR); Bo-Yeon Kwak, Yongin-si (KR)

(73) Assignee: Natural Endotech Co., Ltd., Seoul (KR)

( * ) Notice: Subject to any disclaimer, the term of this patent is extended or adjusted under 35 U.S.C. 154(b) by 0 days.

(21) Appl. No.: 13/258,623

(22) PCT Filed: Mar. 18, 2010

(86) PCT No.: PCT/KR2010/001678
§ 371 (c)(1),
(2), (4) Date: Sep. 22, 2011

(87) PCT Pub. No.: WO2010/110552
PCT Pub. Date: Sep. 30, 2010

(65) Prior Publication Data
US 2012/0015059 A1  Jan. 19, 2012

(30) Foreign Application Priority Data

Mar. 23, 2009 (KR) .................. 10-2009-0024468
Mar. 27, 2009 (KR) .................. 10-2009-0026429
Apr. 9, 2009 (KR) .................. 10-2009-0030643

(51) Int. Cl.
*A61K 36/53* (2006.01)
*A61K 36/00* (2006.01)

(52) U.S. Cl. ......................................... 424/745; 424/725
(58) Field of Classification Search .................. None
See application file for complete search history.

(56) References Cited

FOREIGN PATENT DOCUMENTS

| JP | 2007001972 A | * | 1/2007 |
| KR | 10-0382040 | | 4/2003 |
| KR | 10-0406837 | | 11/2003 |

OTHER PUBLICATIONS

Zhang et al. (2009) C.R. Biologies 332: pp. 816-826.*
Shang et al. (2011) Fitoterapia 82: pp. 716-721.*
Houghten (1999) J. Pharm. Pharmacol. 51: pp. 505-512.*

* cited by examiner

*Primary Examiner* — Chris R Tate
*Assistant Examiner* — Russell Fiebig
(74) *Attorney, Agent, or Firm* — Clark & Elbing LLP

(57) ABSTRACT

Provided is a composition for preventing or treating insomnia. The composition includes, as an active ingredient, extract of *Phlomis umbrosa* Turcz. or a combination thereof with extract of *Polygala tenuifolia* Willd. Particularly, the combination of extract of *Phlomis umbrosa* Turcz. with extract of *Polygala tenuifolia* Willd. enables recovery of the sleep of patients suffering from insomnia nearly to that of normal persons. The composition for treating insomnia uses active ingredients that have been used as Chinese traditional medicines, and thus is safe to the human body.

2 Claims, No Drawings

COMPOSITION FOR PREVENTION OR TREATMENT OF INSOMNIA

Cross-Reference to Related Applications

This application is the U.S. national stage filing under 35 U.S.C. §371 of international application PCT/KR2010/001678, filed Mar. 18, 2010, which claims benefit of Korean Patent Applications 10-2009-0024468, filed Mar. 23, 2009, 10-2009-0026429, filed Mar. 27, 2009, and 10-2009-0030643, filed Apr. 9, 2009.

TECHNICAL FIELD

The present invention relates to a composition for preventing or treating insomnia.

BACKGROUND

It is known that many pathological conditions are caused by insomnia. When physicians evaluate insomnia conditions, they generally assess i) latency to sleep, ii) duration of sleep, iii) unstable patterns of sleep, i.e., frequent nocturnal wakening events, and iv) residual hangover effects, such as morning drowsiness and impaired cognitive and motor functions.

Initial insomnia therapy generally uses central nervous system inhibitors, such as barbiturates. However, such barbiturates are known to cause side effects, including narcolepsy, derangement and depression.

Another category of drugs used for treating insomnia are sedative-hypnotic agents of benzodiazepines. However, such drug species also have side effects, including drug resistance after repeated administration thereof and round insomnia after stopping administration.

Additional drugs used for chemotherapy of insomnia include pyrazolopyrimidine-based sleeping pills, Zolpidem and Zaleplon.

However, most drugs developed for chemotherapy of insomnia hitherto have side effects and particularly cause severe drug intoxication in the case of long-term administration.

Many documents and patent publications are incorporated herein by reference in their entirety to describe clearly the state of the art and the present disclosure.

DETAILED DESCRIPTION OF EMBODIMENTS

The inventor of the present invention has conducted many studies to develop an agent for treating insomnia without side effects. As a result, it has been found that extract of *Phlomis umbrosa* Turcz. or a combination thereof with extract of *Polygala tenuifolia* Willd. enables recovery of the sleep of patients suffering from insomnia nearly to that of normal persons. The present invention based on this finding.

Therefore, an object of the present invention is to provide a composition for preventing or treating insomnia.

Another object of the present invention is to provide a method for preventing or treating insomnia.

Other features and aspects will be apparent from the following detailed description and the claims.

In one aspect, there is provided a composition for preventing, treating or improving insomnia, including extract of *Phlomis umbrosa* Turcz. as an active ingredient.

In another aspect, there is provided a method for preventing or treating insomnia, including administering extract of *Phlomis umbrosa* Turcz. to a subject.

The inventor of the present invention has conducted intensive studies to develop an agent for treating insomnia (or sleeping disorders) without any side effects. As a result, it has been found that extract of *Phlomis umbrosa* Turcz. or a combination thereof with extract of *Polygala tenuifolia* Willd. enables recovery of the sleep of patients suffering from insomnia nearly to that of normal persons.

The composition according to the present invention includes, as an active ingredient, extract of *Phlomis umbrosa* Turcz. or extract of *Polygala tenuifolia* Willd.

One active ingredient, *Phlomis umbrosa* Turcz., is a perennial plant with a typical height of 1 m, has about 5 thickened roots like sweet potatoes, and belongs to Labietae. Traditionally, *Phlomis umbrosa* Turcz. has been known to have pharmacological efficacy in protection of liver and kidney (see: http://www.nanumy.co.kr/folk-remedy/documents/ic5.5-11.html.) The present inventor has found that such extract of *Phlomis umbrosa* Turcz. is effective for improving human sleep.

Another active ingredient, *Polygala tenuifolia* Willd. is a perennial plant with a typical height of 25-40 cm and has been used as a Chinese traditional medicine effective for discharging sputum in acute or chronic bronchitis, pneumonia and laryngitis.

The extract of *Phlomis umbrosa* Turcz. or *Polygala tenuifolia* Willd. used herein is obtained preferably by using, as an extraction solvent, (a) water, (b) C1-C4 hydrous or anhydrous lower alcohol (methanol, ethanol, propanol, butanol, n-propanol, isopropanol and n-butanol, etc.), (c) mixed solvent of the above-mentioned lower alcohol with water, (d) acetone, (e) ethyl acetate, (f) chloroform, (g) 1,3-butylene glycol, (h) hexane, or (i) diethyl ether.

Meanwhile, as known to those skilled in the art, the extract of *Phlomis umbrosa* Turcz. or *Polygala tenuifolia* Willd. may be obtained by using various extraction solvents other than the above-listed solvents while maintaining substantially the same pharmacological effects.

In addition, the extract used herein may include not only the extract obtained by using the above-mentioned solvents but also the extract further subjected to a conventional purification process. Typical examples of such a purification process include separation using an ultrafiltration membrane with a specific cut-off molecular weight, separation using various chromatographic systems (based on size, charge, hydrophobicity or affinity), etc. Fractions obtained by such purification processes may also be included in the scope of the present invention.

The extract according to the present invention may be provided in the form of powder through an additional process, such as distillation under reduced pressure, freeze drying or spray drying.

The composition according to the present invention may use extract of *Phlomis umbrosa* Turcz. or *Polygala tenuifolia* Willd. individually as an active ingredient. However, the composition preferably uses a combination of extract of *Phlomis umbrosa* Turcz. with extract of *Polygala tenuifolia* Willd. as an active ingredient. As demonstrated in the following examples, such a combination of extract of *Phlomis umbrosa* Turcz, with extract of *Polygala tenuifolia* Willd. significantly improves insomnia conditions as compared to each type of extract alone.

When using any one type of extract alone as an active ingredient of the composition according to the present invention, the extract may be present in an amount of 1-99 wt % based on the total weight of the composition.

When using a combination of extract of *Phlomis umbrosa* Turcz. with extract of *Polygala tenuifolia* Willd. as an active ingredient of the composition according to the present invention, each type of extract may be present in an amount of 1-99 wt % based on the total weight of the composition. In addition, when using such a combination, the extract of *Phlomis*

*umbrosa* Turcz. and the extract of *Polygala tenuifolia* Willd. may be present in a weight ratio of 10:90-90:10, preferably 20:80-80:20, more preferably 30:70-70:30, and most preferably 40:60-60:40 (extract of *Phlomis umbrosa* Turcz. : extract of *Polygala tenuifolia* Willd.).

The composition according to the present invention may be provided as a pharmaceutical composition or food composition.

When the composition according to the present invention is provided as a pharmaceutical composition, the pharmaceutical composition includes pharmaceutically acceptable carriers. The pharmaceutically acceptable carrier included in the pharmaceutical composition according to the present invention are those used generally in pharmaceutical formulation, and particular examples thereof include, but are not limited to: lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methyl cellulose, methylhydroxybenzoate, propylhydroxybenzoate, talc, magnesium stearate and mineral oil. In addition to the above, the pharmaceutical composition according to the present invention may further include a lubricant, wetting agent, sweetener, fragrance, emulsifier, suspending agent, preservative, or the like. Suitable pharmaceutically acceptable carriers and formulation thereof are described in detail in *Remington's Pharmaceutical Sciences* (19$^{th}$ ed., 1995).

The pharmaceutical composition according to the present invention may be administered via oral or parenteral routes, and oral administration is preferred.

Adequate dose of the pharmaceutical composition of the present invention may be determined according to various factors, including methods of formulation, administration modes, ages, weights, sex, pathological conditions and diet of patients, administration periods, administration routes, excretion rates and reaction sensitivity. General dose of the pharmaceutical composition of the present invention is 0.01-1000 mg/kg weight in the case of adult patients.

The pharmaceutical composition of the present invention may be formulated by using pharmaceutically acceptable carriers and/or excipients so that it may be provided as a unit dosage form or may be packed in a multi-dose container in a manner generally known to those skilled in the art. Such dosage forms include solutions or suspensions in oil or aqueous media, syrup, emulsion, elixir, powder, flour, granules, tablets, capsules, etc., and may further include a dispersant or stabilizer.

When the composition of the present invention is provided as a food composition, the food composition includes additives generally used in food industry, in addition to extract of *Phlomis umbrosa* Turcz. and extract of *Polygala tenuifolia* Willd. as active ingredients. Particular examples of such additives include proteins, carbohydrates, fat, nutrients, seasoning agents and flavoring agents. Particular examples of the carbohydrates include monosaccharides, such as glucose or fructose; disaccharides, such as maltose, sucrose, oligosaccharides, etc.; polysaccharides, such as currently used sugars, including dextrin and cyclodextrin; and sugar alcohols, such as xylitol, sorbitol, erythritol, etc. As flavoring agents, natural flavoring agents (e.g. thaumatin, stevia extract (e.g. rebaudioside A, glycyrrhizin, etc.)) and synthetic flavoring agents (saccharin, aspartame, etc.) may be used.

In brief, the present invention has the following features and advantages:

(a) The present invention suggests extract of *Phlomis umbrosa* Turcz. and extract of *Polygala tenuifolia* Willd. as an active ingredient for treating insomnia.

(b) Particularly, combination of extract of *Phlomis umbrosa* Turcz. with extract of *Polygala tenuifolia* Willd. enables recovery of the sleep of patients suffering from insomnia to that of normal persons.

(c) The composition for treating insomnia according to the present invention uses active ingredients that have been used as Chinese traditional medicines, and thus is safe to the human body.

EXAMPLES

The examples and experiments will now be described. The following examples and experiments are for illustrative purposes only and not intended to limit the scope of this disclosure.

Example 1

Preparation of Extract of *Phlomis umbrosa* Turcz. and Extract of *Polygala tenuifolia* Willd.

First, 1.5 L of distilled water is added to each of 50 g of *Phlomis umbrosa* Turcz. and 50 g of *Polygala tenuifolia* Willd., purchased from Kyong-dong Market (Korea), followed by heating and extraction at 80-90° C. for 6-12 hours. In this manner, aqueous extract of *Phlomis umbrosa* Turcz. and aqueous extract of *Polygala tenuifolia* Willd. are obtained, each in an amount of 0.7 L. Next, 0.7 L of the thus obtained extract is stored at room temperature. Then, distilled water is added to the remaining medicinal herbs in an amount corresponding to a half of the amount added for the previous extraction, followed by further heating and extraction at 80-90° C. for 6-12 hours. After that, 1L of the extract obtained after the first and the second extraction processes is collected, and subjected to drying under reduced pressure in a freeze dryer (Edwards, USA). Finally, each extract is obtained in the form of powder.

Example 2

Evaluation of Effects of Extract of *Phlomis umbrosa* Turcz. and Extract of *Polygala tenuifolia* Willd. upon Treatment of Insomnia The following test is carried out to evaluate the effect of Extract of *Phlomis umbrosa* Turcz. (Group I), extract of *Polygala tenuifolia* Willd. (Group II), or a combination of extract of *Phlomis umbrosa* Turcz. with extract of *Polygala tenuifolia* Willd. (Group III: a combination of the same amount of both types of extracts) upon treatment of insomnia. The test subjects include male and female adults suffering from insomnia for one year or more. The age of male and female adults is 30-65. Each test group has 20 patients. Administration is carried out orally in a unit dose of 100 mg once a day. The effect of each active ingredient is evaluated at the time of 1 month and 3 months after the administration is started.

Evaluation of the effect of treating insomnia is based on the evaluation of sleep according to St. Mary's Hospital (SMH) Sleep Questionnaire with proven validity and reliability (Ellis BW et al., The St. Mary's Hospital sleep questionnaire: a study of reliability, *Sleep.* 4(1):93-7(1981)). Particularly, the following items are evaluated: (a) latency to sleep (the length of time from the decision to sleep to the onset of sleep); (b) total sleep time at night; and (c) the number of wakening during sleep.

The test results are shown in the following Tables 1a and 1b.

TABLE 1a

Evaluation of Sleep after 1-Month Administration

| Item | Control | Group I (*Phlomis umbrosa* Turcz.) | Group II (*Polygala tenuifolia* Willd.) | Group III (combination) |
|---|---|---|---|---|
| Latency to sleep (min.) | 80.1 | 55.5 | 63.4 | 30.1 |
| Total sleep time at night (min.) | 270.2 | 294.6 | 292.8 | 320.8 |
| Number of wakening during sleep | 3.1 | 2.1 | 2.8 | 1.7 |

TABLE 1b

Evaluation of Sleep after 3-Month Administration

| Item | Control | Group I (*Phlomis umbrosa* Turcz.) | Group II (*Polygala tenuifolia* Willd.) | Group III (combination) |
|---|---|---|---|---|
| Latency to sleep (min.) | 80.1 | 50.4 | 58.7 | 20.2 |
| Total sleep time at night (min.) | 270.2 | 309.1 | 323.6 | 375.5 |
| Number of wakening during sleep | 3.1 | 1.9 | 2.5 | 0.8 |

As can be seen from Table 1a, when the extracts according to the present invention are administered for 1 month, they clearly improve all of the three evaluation items. Particularly, in the case of the combination of extract of *Phlomis umbrosa* Turcz. with extract of *Polygala tenuifolia* Willd., all of the three evaluation items are improved significantly.

When the extracts according to the present invention are administered for 3 months, insomnia conditions are improved more significantly (see Table 1b). Particularly, administration of the combination of extract of *Phlomis umbrosa* Turcz. with extract of *Polygala tenuifolia* Willd. improves the evaluation items nearly to normal conditions.

While the present invention has been described with respect to the specific embodiments, it will be apparent to those skilled in the art that various changes and modifications may be made without departing from the spirit and scope of the invention as defined in the following claims.

What is claimed is:

1. A method for treating insomnia, comprising administering a composition comprising an effective amount of an extract of *Phlomis umbrosa* Turcz. to a subject suffering from insomnia.

2. The method according to claim 1, which further comprises administering to said subject an effective amount of extract of an *Polygala tenuifolia* Willd.

* * * * *